United States Patent [19]

Brodie et al.

[11] 4,235,893

[45] Nov. 25, 1980

[54] ESTER DERIVATIVES OF 4-HYDROXY-4-ANDROSTENE-3,17-DIONE AND A METHOD FOR INHIBITING ESTROGEN BIOSYNTHESIS

[76] Inventors: Angela M. H. Brodie; Harry J. Brodie, both of 8373 Reservoir Rd., Fulton, Md. 20759; David A. Marsh, 13 Edgewater Ave., Shrewsbury, Mass. 01545

[21] Appl. No.: 903,551

[22] Filed: May 8, 1978

[51] Int. Cl.$^3$ .............................................. A61K 31/56
[52] U.S. Cl. .................................. 424/243; 260/397.4; 260/239.55 R
[58] Field of Search ..................... 260/397.4; 424/243

[56] References Cited

U.S. PATENT DOCUMENTS 3,060,201  10/1962  Camerino et al. ................ 260/397.4

OTHER PUBLICATIONS

Chem. Abstracts (1976), vol. 85, Par. 61351s.

*Primary Examiner*—Elbert L. Roberts
*Attorney, Agent, or Firm*—Davis, Hoxie, Faithfull & Hapgood

[57] ABSTRACT

This invention relates to ester derivatives of 4-hydroxy-4-androstene-3,17-dione (4-OH-4-A), including the acetate, heptanoate, dodecanoate, hemisuccinate and benzoate esters of 4-OH-4-A.

This invention also relates to a method of using the esters in the inhibition of estrogen biosynthesis.

6 Claims, No Drawings

ESTER DERIVATIVES OF 4-HYDROXY-4-ANDROSTENE-3,17-DIONE AND A METHOD FOR INHIBITING ESTROGEN BIOSYNTHESIS

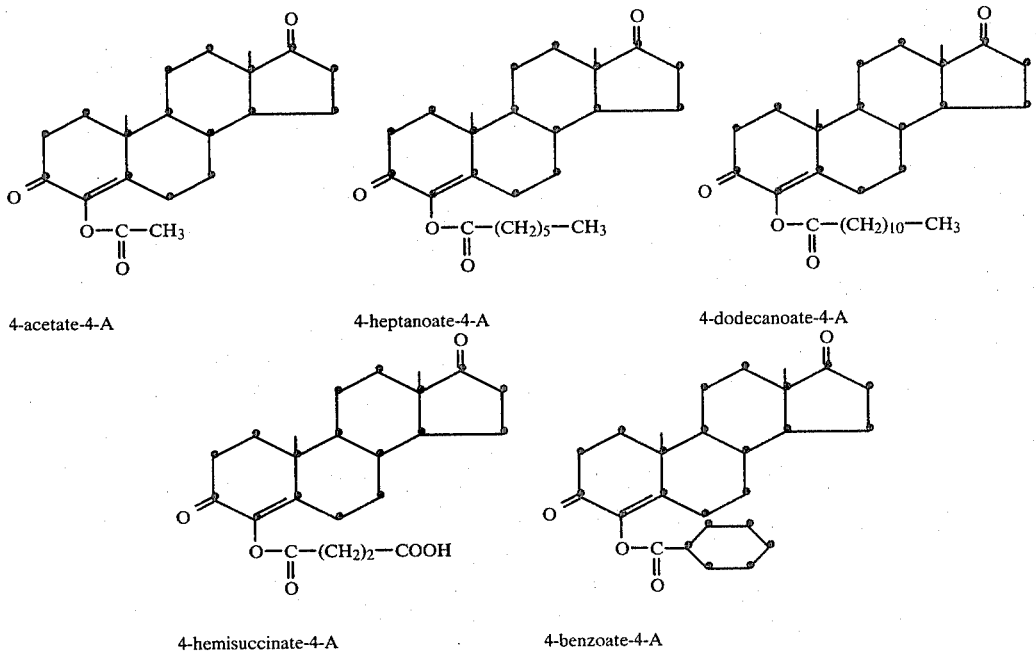

4-acetate-4-A 4-heptanoate-4-A 4-dodecanoate-4-A

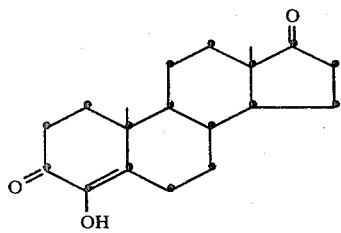

4-hemisuccinate-4-A

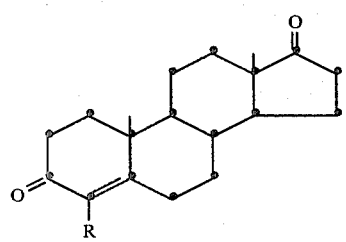

4-benzoate-4-A

This invention relates to ester derivatives of 4-hydroxy-4-androstene-3,17-dione (4-OH-4-A) and their use as inhibitors of estrogen biosynthesis. The formula (Formula A) of 4-OH-4-A is:

(A)

The general formula (Formula B) of the novel ester compounds of this invention is as follows, where R is selected from the group consisting of straight-chain, saturated monocarboxylates with 2-12 carbon atoms; hemisuccinate; and benzoate:

(B)

Representative of the compounds embraced by Formula B, and described in detail herein, are the following esters: the acetate ester (4-acetate-4-A), the heptanoate ester (4-heptanoate-4-A), the dodecanoate ester (4-dodecanoate-4-A), the hemisuccinate ester (4-hemisuccinate-4-A), and the benzoate ester (4-benzoate-4-A). The formulas of these compounds are:

In recent years the mechanism of estrogen biosynthesis has been elucidated. As this mechanism became better understood, the opportunity was presented for designing compounds that would inhibit the biosynthesis of estrogen. Such inhibitors could be useful in controlling estrogen-dependent phenomena. Of particular importance was the possibility of controlling the estrogen-dependent phenomena of fertility and breast cancer.

A wide variety of steriod compounds, as well as selected non-steroids, were examined as possible inhibitors of estrogen biosynthesis. See W. C. Schwarzel, W. Kruggel and H. J. Brodie, *Endocrinology*, 92, 866 (1973), wherein 1,4,6-androstatriene-3,17-dione, 4-androstene-3,6,17-trione, and 4-estrene-3,17-dione were selected from a large group of tested compounds as being effective inhibitors of estrogen biosynthesis.

Later, detailed experimental results were reported for 4-hydroxy-4-androstene-3,17-dione (4-OH-4-A), a compound also found to be an effective inhibitor of estrogen biosynthesis. A. M. H. Brodie, W. C. Schwarzel, A. A. Shaikh, and H. J. Brodie, *Endrocrinology*, 100, 1684 (1977). Biosynthesis inhibition by 4-OH-4-A was demonstrated in vitro with studies of rat ovarian and human placental microsomes, and in vivo (using rats) with studies of blood estrogen levels and the estrogen-related processes of ovulation, implantation, and mammary tumor growth.

Inhibition of estrogen biosynthesis is generally believed to result from the ability of the inhibiting compound to block or competitively interfere with aromatase (estrogen synthetase), an enzyme essential to the biosynthesis of estrogen.

The novel esters claimed herein are effective inhibitors of estrogen biosynthesis. In vivo rat studies have demonstrated that biosynthesis inhibition by 4-acetate-4-A leads to lower ovarian estrogen secretion. The result is a pronounced anti-fertility effect due to inhibition of mating, ovulation and implantation. In vivo experiments showing these results are summarized in Examples VIII and IX. Table I in Example VIII shows the inhibitory effect of 4-acetate-4-A on mating in rats. Table II in Example IX shows the inhibitory effect of 4-acetate-4-A on implantation in mated rats. Both results ae attributable to inhibition of estrogen biosynthesis and demonstrate the importance of 4-acetate-A for use as an anti-fertility agent.

In vivo studies showing the suppression of estrogen-dependent mammary tumors in rats by treatment with 4-acetate-4-A are summarized in Example X. The significant regression of tumors in the sample group upon treatment with 4-acetate-4-A, as compared to that of the control group, is again attributatable to the inhibition of estrogen biosynthesis by 4-acetate-4-A.

4-acetate-4-A has been found, in rat studies, to be a superior inhibitor of estrogen biosynthesis in that, unlike 4-OH-4-A, it may be administered as a skin implant. Such administration permits continuous, uniform release of the compound into the living system. 4-OH-4-A, by contrast, does not diffuse as well from the implant and must be administered by multiple daily injections. This advantage of 4-acetate-4-A is surprising in that 4-OH-4-A, being less polar than 4-acetate-4-A (as shown by thin layer chromatography), would be expected to leach more readily from the nonpolar implant.

4-hemisuccinate-4-A has similarly been shown by both in vitro and in vivo experiments to possess marked ability to inhibit estrogen biosynthesis. The Contraceptive Development Branch of the National Cancer Institute has requested that samples of 4-hemisuccinate-4-A be prepared for evaluation as a possibly orally active compound.

It is expected that the other compounds claimed herein—including the heptanoate, dodecanoate and benzoate esters—will display inhibitory activity similar to that of 4-acetate-4-A and 4-hemisuccinate-4-A. This expectation has been borne out for 4-heptanoate-4-A in in vitro studies. Furthermore, the longer chain and benzoate esters have an important advantage over 4-OH-4-A where administration is by injection. Since these esters are more lipophilic in nature, release from body fat following injection is much slower. As a consequence, multiple daily injections, which are required for administration of 4-OH-4-A, should not be necessary when the benzoate or longer chain esters are used.

The esters of this invention may be prepared by reaction of 4-OH-4-A with an appropriate esterifying agent. 4-OH-4-A in turn may be prepared according to known methods, R. D. Burnett and D. N. Kirk, *J. Chem. Soc. Perkins Trans. I,* 1830 (1973), or by an improved method, employing much lower concentration of reactant hydroxide, as illustrated in Example I.

The following examples illustrate the invention:

EXAMPLE I. Preparation of 4-OH-4-A.

4-androstene-3,17-dione (5 g, Searle Chemicals) was dissolved in 200 ml of methanol A.R. and cooled to 0° C. 17 ml of 30% $H_2O$ (ice cold) was added to the magnetically stirred solution (in an ice bath) and 9 ml of ice cold 2% NaOH (resultant concentration of hydroxide in reaction mixture 0.02 M) was added. The mixture was stirred for 30 min. The reaction was stopped and allowed to stand at 5° C. without stirring. After 22 hours the reaction mixture was poured into 1400 ml of ice water with vigorous stirring. After 15 minutes, the product was filtered and washed with water. The yield of epoxide, 4,5-epoxyandrostane-3,17-dione, was 4.2 g (80% yield) when dried to a constant weight. GC/MS and pmr data showed the product was pure and composed of approximately 66% β-isomer and 34% α-isomer. Analysis by tlc (benzene:ethyl acetate, 3:2, v.v.) showed a single non-UV absorbing spot identical in $R_f$ to that of a known sample of the epoxide.

4 g of epoxide was dissolved without further purification in 100 ml of a cooled mixture of concentrated $H_2SO_4$ in glacial acetic acid (2:98). The solution was warmed to room temperature and after 2.5 hours at that temperature was poured into 900 ml ice water and allowed to stand for 15 min. The product 4-OH-4-A was filtered and dried to constant weight under reduced pressure. The crude product weighed 2.3 g (58% yield) and showed less than 5% impurity by GC/MS. The product twice recrystallized from ethyl acetate was obtained in 43% yield (1.7 g).

EXAMPLE II. Preparation of 4-acetate-4-A.

2.34 g of crude 4-OH-4-A was dissolved in 8 ml of pyridine and cooled in an ice bath. 5 ml of cold acetic anhydride was added and the reaction mixture was allowed to stand overnight at room temperature. The solvents were removed under reduced pressure and 25 ml of CCl was added and evaporated four times in sequence. The residue was triturated with 9 ml of methanol:acetone (5:4) which was then removed by filtration. The residue was washed with 5 ml of methanol to give 1.26 g 4-acetate-4-A as white solid, m.p. 180.5°–183.5° C. (47.2% yield). A second crop was obtained, weighing 0.22 g (8.2% additional yield, m.p. 178°–180° C.). The first crop was dissolved in acetone, filtered, and evaporated to give typical yields of analytically pure material of 46–52% (based on 4-OH-4-A). Alternatively, the first and second crops were combined and recrystallized once from ethyl acetate to give 1.15 g (43% yield) of analytically pure material (elemental analysis 73.10% C., 8.28% H; calc. 73.22% C., 8.19% H).

EXAMPLE III. Preparation of 4-heptanoate-4-A.

1 g of 4-OH-4-A was dissolved in 25 ml of ethanol-free chloroform containing 0.29 ml pyridine. A solution of 0.50 ml heptanoyl chloride in 25 ml of chloroform was added. After stirring overnight, an additional 0.3 ml of pyridine was added and the reaction was stirred for an additional 24 hours. The solvent was removed under nitrogen and the residue dissolved in $CHCl_3$. The solution was washed three times with concentrated $NaHCO_3$ solution, three times with water, two times with 0.25 N HCl and two times with water. The solution was dried over anhydrous $Na_2SO_4$, filtered, evaporated to an oil and placed under a nitrogen stream until crystals of 4-heptanoate-4-A formed. The crystals were dissolved in a minimum amount of methanol, allowed to crystallize at 8° C., filtered and washed with cold methanol, yielding 430 mg (31%) of white crystals.

EXAMPLE IV. Preparation of 4-dodecanoate-4-A.

4-dodecanoate-4-A was prepared in like manner to the preparation of 4-heptanoate-4-A in Example III, with the exception of using lauroyl chloride in place of heptanoyl chloride. 4-dodecanoate-4-A was obtained in 61% yield.

EXAMPLE V. Preparation of 4-hemisuccinate-4-A.

A solution of 4.4 g of 4-OH-4-A, 8.8 g of succinic anhydride and 50 ml of pyridine was refluxed under nitrogen for 160 hours. After cooling to room temperature, the reaction was filtered and washed with chloroform. The filtrate was poured into 250 ml of ice cold 0.25 N HCl and shaken. The organic layer was separated and washed four times with 200 ml of 1 N HCl. The combined aqueous layers were washed two times with 250 ml of CHCl$_3$, and the organic fractions were combined and dried over anhydrous Na$_2$SO$_4$. The solution was filtered and evaporated in vacuo to an oil. The oil was twice chromatographed on silica using benzene:ethyl acetate:acetic acid 33:66:1. The resultant oil was treated with charcoal in ethanol and carefully evaporated to yield 4-hemisuccinate-4-A as a solid. The solid was dried in a vacuum oven at 60° C. and recrystallized from ethyl acetate/cyclohexane to give 1.35 g product.

EXAMPLE VI. Preparation of 4-benzoate-4-A.

4-benzoate-4-A was prepared in like manner to the preparation of 4-OH-4-A heptanoate in Example III, with the exception of using benzoyl chloride in place of heptanoyl chloride. The product was recrystallized from methanol to give a white solid in 48% yield.

EXAMPLE VII. Preparation of other novel esters.

The other claimed esters may be prepared in like manner to the preparation of 4-heptanoate-4-A in Example III. However, the acid chloride that corresponds to the monocarboxylate group of the ester being prepared should be used in place of heptanoyl chloride.

EXAMPLE VIII. In vivo experiment showing the effect of 4-acetate-4-A on mating in rats.

Procedure

Female rats showing at least 2 consecutive 4-day cycles were used. On the day of diestrus I, a silastic wafer, was inserted under the dorsal skin of each rat. The wafer, about 25 mm in diameter and 1 mm thick, was prepared by polymerizing 0.5 g of Corning medical grade Silastic 382 with 75 mg 4-acetate-4-A, using stannous octoate catalyst. Each female was housed with 2 fertile males until mating occurred. Control animals were treated with same except that 4-acetate-4-A was omitted from the wafer.

Results

Table I shows the inhibitory effect of 4-acetate-4-A on mating in rats.

Table I

| Treatment | Number of Animals | Number of animals mating on a given day | | | | |
|---|---|---|---|---|---|---|
| | | 1st | 2d | 6th | 7th | 15th day |
| Control | 8 | 8 | 0 | 0 | 0 | 0 |
| 4-acetate-4-A | 8 | 0 | 1 | 2 | 2 | 3 |

EXAMPLE IX. In vivo experiment showing the effect of 4-acetate-4-A on implantation in mated rats.

Procedure

Injections of 4-acetate-4-A in a suspending vehicle were begun at 0800 hr on Day 2 of pregnancy, and repeated thereafter at 1200, 1600 and 2000 hrs. as 1/6 daily dose, and at 2400 hr as 2/6 daily dose. The daily does was 100 mg of 4-acetate-4-A per kg of body weight. Control animals were treated the same except that only the suspending vehicle was injected.

Results

Table II shows the inhibitory effect of 4-acetate-4-A on implantation in mated rats.

Table II

| Treatment | Number of animals | Animals without implants | Average number of normal-sized implants/ animal | Average number of small (<2.4 mm) implants/ animal | Number of animals affected by treatment |
|---|---|---|---|---|---|
| Control | 7 | 0 | 14 | 0 | 0 |
| 4-acetate-4-A | 7 | 4 | 1.7 | 1.4 | 7 |

EXAMPLE X. In vivo experiment showing the effect of of 4-acetate-4-A on mammary tumors in rats.

Procedure

Estrogen-dependent mammary tumors where induced in rats with DMBA. Prior to treatment the 7 sample group rats had 23 tumors; the 6 control group rats had 17 tumors. During the initial treatment period the number of tumors increased to 28 for the sample group, 24 for the control group.

The sample group was treated with implanted wafers containing 0.5 g silastic and 150 mg 4-acetate-4-A. The sample group was also treated twice daily for 4 weeks with sc injections of 4-acetate-4-A (2.5 mg/100 g animal) in a suspending vehicle. The control was treated the same except that 4-acetate-4-A was omitted from the wafers and the injection.

Results

After 4 weeks of treatment the sample group showed 64% of tumors completely regressed and another 32% regressed to less than ½ their pretreatment size. After the same period of time the control group showed 0% tumors completely regressed and 24% regressed to less than ½ their pretreatment size.

The physical characteristics of esters representative of those claimed herein are summarized as follows:

4-acetate-4-A is a white crystalline solid, recrystallizable from ethyl acetate, with the following properties: mp 184°-184.5° C. (uncorr.); uv(MeOH) $\lambda$ max=248 nm ($\epsilon$ 14,500); ir (KBr, cm$^{-1}$) 2941, 2873, 1754, 1730, 1678, 1623, 1449, 1362, 1215, 1195; 100 MHz pmr (CDCl$_3$, $\delta$) 0.90 (s,18-CH$_3$), 1.28 (s,19-CH$_3$), 2.24 (s,CH$_3$CO$_2$); R$_f$ 0.22 (benzene:ethyl acetate, 3:1, silica).

4-heptanoate-4-A is a white crystalline solid with the following properties: mp 74.5°-75.2° C.; uv (MeOH) $\lambda$ max=246 nm ($\epsilon$ 13,500); ir (KBr, cm$^{-1}$) 2959, 2874, 1757, 1742, 1689, 1208, 1101; 100 MHz pmr (CDCl$_3$, $\delta$) 0.87-0.90 [complex, 6, 18-CH$_3$ and (CH$_2$)$_n$ CH$_3$], 1.26 [complex, 9, 19-CH$_3$ and (CH$_2$)$_3$];GC one peak; MS 302 (MW for 4-OH-4-A).

4-dodecanoate-4-A is an oil with the following properties: uv (MeOH) $\lambda$ max=247 nm ($\epsilon$ 13,200); ir (neat on KBr, cm$^{-1}$) 2969, 2892, 1764, 1746, 1695, 1634, 1469, 1454, 1211, 1111, 1021; 100 MHz pmr (CDCl$_3$, $\delta$) 0.89 (m, 6, 18-CH$_3$+long chain-CH$_3$), 1.26 (complex, 23, [CH$_2$]$_{10}$+19-CH$_3$).

4-hemisuccinate-4-A is a white crystalline solid with the following properties: mp 159°-164° C.; uv (MeOH)

λ max=245 nm, (ε=12,180); ir (KBr, cm$^{-1}$) 3125, 2940, 2855, 1730, 1655, 1620, 1170, 1145; 100 MHz pmr (CDCl$_3$, δ) 0.91 (s, 18-CH$_3$), 1.28 (s, 19-CH$_3$), 2.81 [t, 4, (0)CCH$_2$CH$_2$C(0)], 8.90 (broad, COOH); GC one peak; MS=302 (MW for 4-OH-4-A).

4-benzoate-4-A is a white crystalline solid with the following properties: mp 137.5°-138.5° C.; ir (KBr, cm$^{-1}$) 2976, 2890, 1742, 1692, 1631, 1271, 1261, 1238, 1094, 1071, 714; 100 MHz pmr (CDCl$_3$, δ) 0.92 (s, 18-CH$_3$), 1.32 (s, 19-CH$_3$), 7.56 (m,3, aromatic), 8.16 (doublet, 2, aromatic).

We claim:

1. A method of inhibiting estrogen biosynthesis using as an inhibitor a compound having the general formula

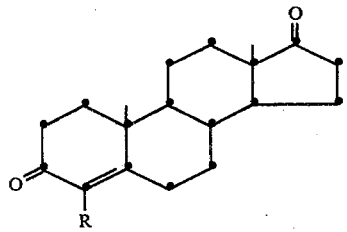

wherein R is selected from the group consisting of straight-chain, saturated monocarboxylates containing 2–12 carbon atoms; hemisuccinate; and benzoate.

2. A method as in claim 1, wherein R is acetate.

3. A method as in claim 1, wherein R is heptanoate.

4. A method as in claim 1, wherein R is dodecanoate.

5. A method as in claim 1, wherein R is hemisuccinate.

6. A method as in claim 1, wherein R is benzoate.

* * * * *